United States Patent [19]

Van den Eynde et al.

[11] Patent Number: 6,069,001
[45] Date of Patent: *May 30, 2000

[54] ISOLATED, TRUNCATED NUCLEIC ACID MOLECULES WHICH CODE FOR GAGE TUMOR REJECTION ANTIGEN, THE TUMOR REJECTION ANTIGEN, AND USES THEREOF

[75] Inventors: Benoit Van den Eynde; Olivier DeBacker; Thierry Boon-Falleur, all of Brussels, Belgium

[73] Assignee: Ludwig Institute for Cancer Research, New York, N.Y.

[ * ] Notice: This patent is subject to a terminal disclaimer.

[21] Appl. No.: 08/602,039

[22] Filed: Feb. 15, 1996

Related U.S. Application Data

[60] Division of application No. 08/370,648, Jan. 10, 1995, Pat. No. 5,648,226, which is a continuation-in-part of application No. 08/250,162, May 27, 1994, Pat. No. 5,610,013, which is a continuation-in-part of application No. 08/096,039, Jul. 22, 1993, abandoned.

[51] Int. Cl.[7] .................................................... C12N 15/12
[52] U.S. Cl. ................. 435/252.3; 435/69.3; 435/320.1; 530/395; 536/23.3
[58] Field of Search ........................ 536/23.3; 435/320.1, 435/252.3, 69.3; 530/328, 300, 395

[56] References Cited

U.S. PATENT DOCUMENTS 5,610,013  3/1997  Van Den Eynde et al. ................. 435/6
5,648,226  7/1997  Van Den Eynde et al. ........... 435/7.24

FOREIGN PATENT DOCUMENTS

WO9411738  5/1994  WIPO .

OTHER PUBLICATIONS

Parham, P. et al., Immunol. Rev. 143:141–180, "The origins of HLA–A, –B, –C polymorphism", 1995.

Falk, et al., "Allele–specific peptide ligand motifs of HLA–C molecules", Proc. Natl. Acad. USA 90: 12005–12009 (Dec. 1993).

Rammensee, et al., "MHC Ligands and Peptide Motifs: First Listing", Immunogenetics 41: 178–228 (1995).

*Primary Examiner*—Thomas M. Cunningham
*Attorney, Agent, or Firm*—Fulbright & Jaworski LLP

[57] ABSTRACT

A new family of tumor rejection antigen precursors, and the nucleic acid molecules which code for them, are disclosed. These tumor rejection antigen precursors are referred to as GAGE tumor rejection antigen precursors, and the nucleic acid molecules which code for them are referred to as GAGE coding molecules. Various diagnostic and therapeutic uses of the coding sequences and the tumor rejection antigens, and their precursor molecules are described. Tumor rejection antigens are also shown.

13 Claims, 7 Drawing Sheets

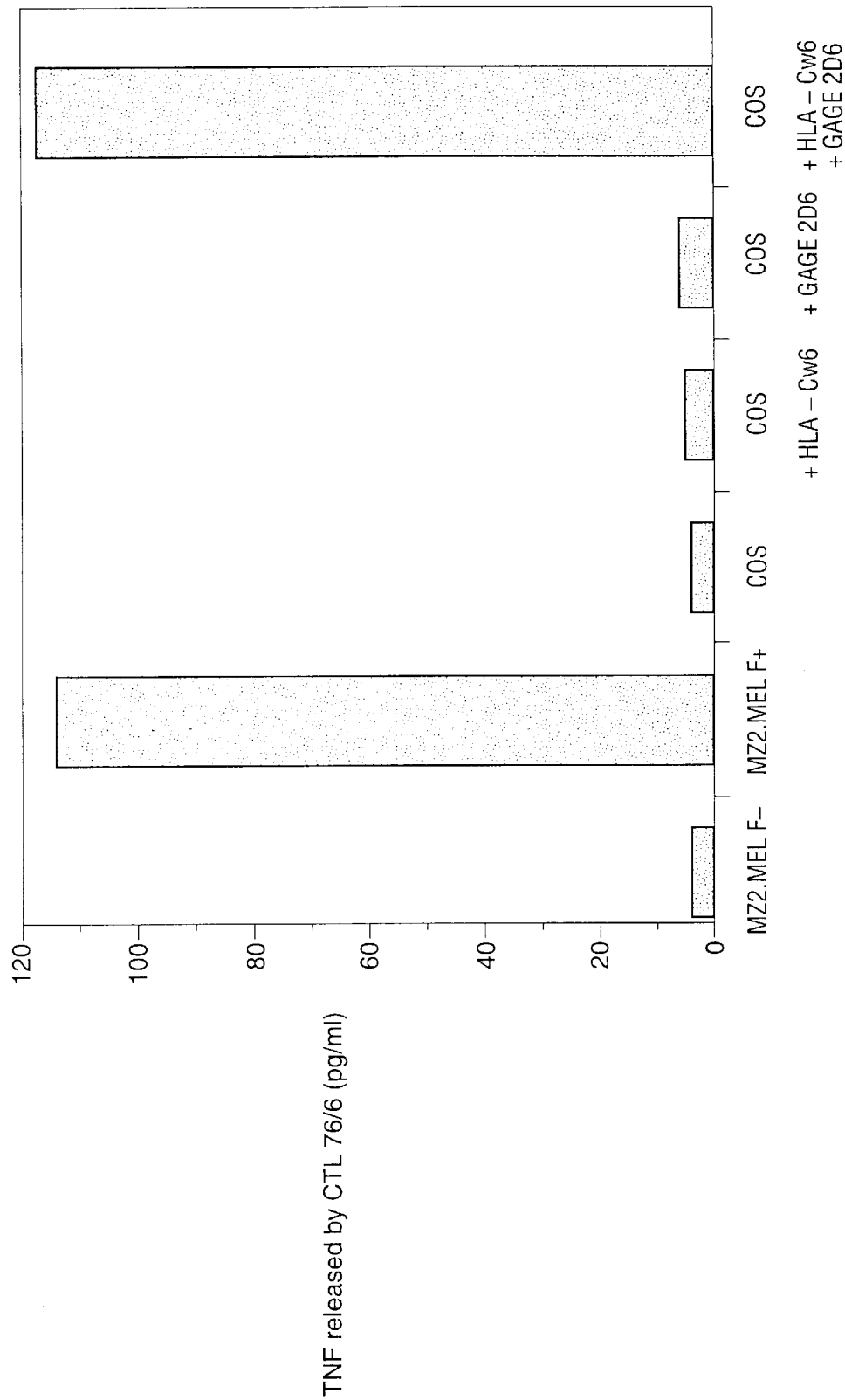

FIG. 4A

[Sequence alignment figure showing GAGE-1 through GAGE-6 nucleotide sequences with VDE 43 and VDE 44 regions indicated]

```
                Antigenic
                 Peptide
GAGE-1  MS-WRGRST-YRPRPRRRYV EPPEMI GPMRPEQFSDEVEPATPEEGEPATQ RQDPAAAQEGEDEGASAGQGPKPEA     7
GAGE-2  MS-WRGRST-YRPRPRRRYV EPPEMI GPMRPEQFSDEVEPATPEEGEPATQ RQDPAAAQEGEDEGASAGQGPKPEA     7
GAGE-3  MNLSRGKST YWPRPRRRYV QPPEMI GPMRPEQFSDEVEPATPEEGEPATQ RQDPAAAQEGEDEGASAGQGPKPEA     7
GAGE-4  MS-WRGRST YWPRPRRRYV QPPEMI GPMRPEQFSDEVEPATPEEGEPATQ RQDPAAAQEGEDEGASAGQGPKPEA     7
GAGE-5  MS-WRGRST YWPRPRRRYV PPEVI  GPMRPEQFSDEVEPATPEEGEPATQ RQDPAAAQEGEDEGASAGQGPKPEA     7
GAGE-6  MS-WRGRST YWPRPRRRYV QPPEVI GPMRPEQFSDEVEPATPEEGEPATQ RQDPAAAQEGEDEGASAGQGPKPEA     7

GAGE-1  DSQEQGHPQTGCECEDGPDGQEMDP PNPEEVKTPEEEMRSHYVAQTGILW LLMNNCFLMLSPRKP   13
GAGE-2  HSQEQGHPQTGCECEDGPDGQEMDP PNPEEVKTPEEGEKQSQC--------------------     11
GAGE-3  DSQEQGHPQTGCECEDGPDGQEMDP PNPEEVKTPEEGEKQSQC--------------------     11
GAGE-4  DSQEQGHPQTGCECEDGPDGQEMDP PNPEEVKTPEEGEKQSQC--------------------     11
GAGE-5  DSQEQGHPQTGCECEDGPDGQEMDP PNPEEVKTPEEGEKQSQC--------------------     11
GAGE-6  DSQEQGHPQTGCECEDGPDGQEVDP PNPEEVKTPEEGEKQSQC--------------------     11
```

ISOLATED, TRUNCATED NUCLEIC ACID MOLECULES WHICH CODE FOR GAGE TUMOR REJECTION ANTIGEN, THE TUMOR REJECTION ANTIGEN, AND USES THEREOF

RELATED APPLICATION

This application is a Divisional of Ser. No. 08/370,648 filed Jan. 10, 1995 now U.S. Pat. No. 5,648,226 which in turn is a continuation-in-part of Ser. No. 08/250,162 filed May, 27, 1994, now U.S. Pat. No. 5,610,013 which is a continuation-in-part of Ser. No. 08/096,039 filed Jul. 22, 1993 (abandoned).

FIELD OF THE INVENTION

This invention relates to a nucleic acid molecule which codes for a tumor rejection antigen precursor. More particularly, the invention concerns genes, whose tumor rejection antigen precursor is processed, inter alia, into at least one tumor rejection antigen that is presented by HLA-Cw6 molecules. The genes in question do not appear to be related to other known tumor rejection antigen precursor coding sequences. The invention also relates to peptides presented by the HLA-Cw6 molecules, and uses thereof.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992). Also see Engelhard, Ann. Rev. Immunol. 12: 181–207 (1994).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs cytolytic T lymphocytes, or "CTLs" hereafter. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also, see U.S. patent application Ser. No. 807,043, filed Dec. 12, 1991, now U.S. Pat. No. 5,342,774.

In U.S. patent application Ser. No. 938,334 now U.S. Pat. No. 5,405,940, the disclosure of which is incorporated by reference, it is explained that the MAGE-1 gene codes for a tumor rejection antigen precursor which is processed to nonapeptides which are presented by the HLA-A1 molecule. The reference teaches that given the known specificity of particular peptides for particular HLA molecules, one should expect a particular peptide to bind to one HLA molecule, but not to others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 008,446, filed Jan. 22, 1993 and incorporated by reference, the fact that the MAGE-1 expression product is processed to a second TRA is disclosed. This second TRA is presented by HLA-C clone 10 molecules. The disclosure shows that a given TRAP can yield a plurality of TRAs.

U.S. patent application Ser. No. 994,928, filed Dec. 22, 1992, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 and incorporated by reference herein, an unrelated tumor rejection antigen precursor, the so-called "BAGE" precursor is described. The BAGE precursor is not related to the MAGE family.

The work which is presented by the papers, patent, and patent applications cited supra deals, in large part, with the MAGE family of genes, and the unrelated BAGE gene. It has now been found, however, that additional tumor rejection antigen precursors are expressed by cells. These tumor rejection antigen precursors are referred to as "GAGE" tumor rejection antigen precursors. They do not show homology to either the MAGE family of genes or the BAGE gene. Thus the present invention relates to genes encoding such TRAPs, the tumor rejection antigen precursors themselves as well as applications of both.

The invention is elaborated upon further in the disclosure which follows.

BRIEF DESCRIPTION OF THE FIGURES

FIG. 2 shows tumor necrosis factor ("TNF") release assays obtained with various transfectants and controls.

FIGS. 4A and B present an alignment of the cDNAs of the six GAGE genes (SEQ ID NOS: 1 and 14–18) discussed herein. In the figure, identical regions are surrounded by boxes. Translation initiation sites and stop codons are also indicated. Primers, used in polymerase chain reaction as described in the examples, are indicated by arrows.

FIG. 5 sets forth the alignment of deduced amino acid sequences for the members of the GAGE family (encoded by SEQ ID NOS:1 and 14–18). Identical regions are shown by boxes, and the antigenic peptide of SEQ ID NO: 4, is shown.

DETAILED DESCRIPTION OF PREFERRED EMBODIMENTS

Example 1

Figure 1A:
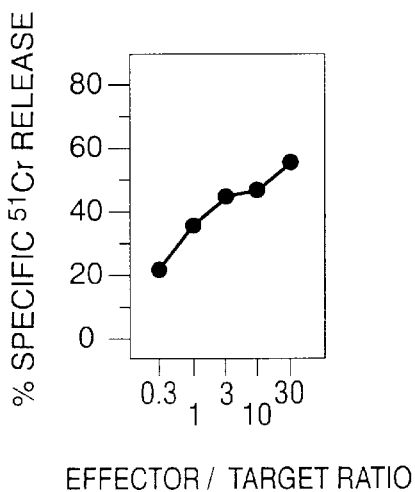
FIGS. 1A, B, C, and D set forth lysis studies using CTL clone 76/6.
Figure 1B:
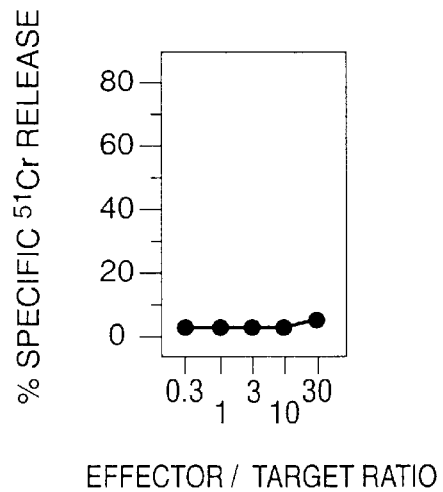
Figure 1C:
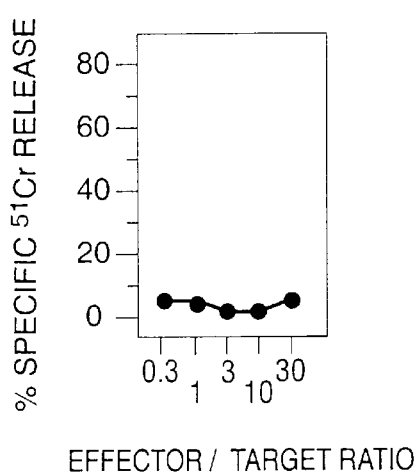
Figure 1D:
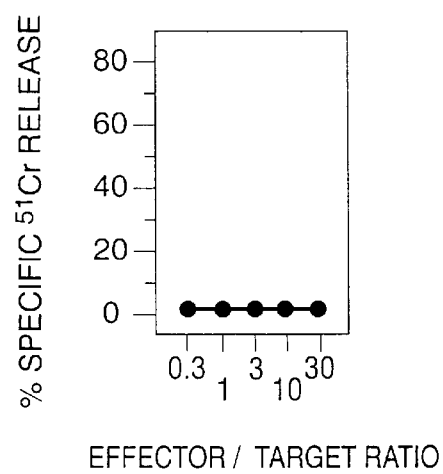

A melanoma cell line, MZ2-MEL was established from melanoma cells taken from patient MZ2, using standard methodologies. This cell line is described, e.g., in PCT Application PCT/US92/04354, filed May 22, 1992, published Nov. 26, 1992, and incorporated by reference in its entirety. Once the cell line was established, a sample thereof was irradiated, so as to render it non-proliferative. These irradiated cells were then used to isolate cytolytic T cell clones ("CTLs") specific thereto.

A sample of peripheral blood mononuclear cells ("PBMCs") was taken from patient MZ2, and contacted to the irradiated melanoma cells. The mixture was observed for lysis of the melanoma cells, which indicated that CTLs specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 8% CO$_2$ atmosphere.

Plates were centrifuged again, and 100 ul aliquots of supernatant were collected and counted. Percentage of $^5$Cr release was calculated as follows:

$$\% \; ^{51}\text{Cr release} = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology. The CTL clone MZ2-CTL 76/6 was thus isolated. The clone is referred to as "76/6" hereafter.

The same method was used to test target K562 cells, as well as the melanoma cell line. FIG. 1 shows that this CTL clone recognizes and lyses the melanoma cell line, i.e. MZ2-MEL but not K562. The clone was then tested against other melanoma cell lines and autologous EBV-transformed B cells in the same manner described supra. FIG. 1 shows that autologous B cells, transformed by Epstein Barr Virus ("EBV") were not lysed, and that while MZ2-MEL 3.0 was lysed by CTL clone 76/6, the cell line MZ2-MEL.4F$^-$, a variant which does not express antigen F, was not. Hence, the clone appears to be specific for this antigen.

The results presented supra are inconclusive as to which HLA molecule presents the TRA. The lysed cell line, i.e., MZ2-MEL, is known to express HLA-A1, HLA-A29, HLA-B37, HLA-B44, HLA-Cw6, and HLA-C clone 10. In experiments not reported here but which followed the protocol of this example, a subline of MZ2-MEL was tested, which had lost expression of HLA molecules A29, B44, and C clone 10. The subline was lysed, thus indicating that the presenting molecule should be one of Al, B37, or Cw6.

Example 2

Further studies were carried out to determine if 76/6 also produced tumor necrosis factor ("TNF") when contacted with target cells. The method used was that described by Traversari et al., Immunogenetics 35: 145–152 (1992), the disclosure of which is incorporated by reference. Briefly, samples of the CTL line were combined with samples of a target cell of interest in culture medium. After 24 hours, supernatant from the cultures was removed, and then tested on TNF-sensitive WEHI cells. Cell line MZ2MEL.43, a subclone of the MZ2-MEL cell line discussed supra as well as in the cited references, gave an extremely strong response, and was used in the following experiments.

Example 3

The results from Example 2 indicated that MZ2.MEL.43 presented the target antigen of interest. As such, it was used as a source of total mRNA to prepare a CDNA library.

Total RNA was isolated from the cell line. The mRNA was isolated using an oligo-dT binding kit, following well recognized techniques. Once the MRNA was secured, it was transcribed into cDNA, via reverse transcription, using an oligo dT primer containing a NotI site, followed by second strand synthesis. The CDNA was then ligated to a BstXI adaptor, digested with NotI, size fractionated on a Sephacryl S-500 HR column, and then cloned, undirectionally, into the BstXI and Not I sites of pcDNAI/Amp. The recombinant plasmid was then electroporated into DH5α E. coli bacteria. A total of 1500 pools of 100 recombinant bacteria were seeded in microwells. Each contained about 100 cDNAs, because nearly all bacteria contained an insert.

Each pool was amplified to saturation and plasmid DNA was extracted by alkaline lysis and potassium acetate precipitation, without phenol extraction.

Example 4

Following preparation of the library described in Example 3, the cDNA was transfected into eukaryotic cells. The transfections, described herein, were carried out in duplicate. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 50 μl/well of DMEM medium containing 10% Nu serum, 400 μg/ml DEAE-dextran, and 100 μM chloroquine, plus 100 ng of the plasmids. As was indicated supra, the lysis studies did not establish which HLA molecule presented the antigen. As a result, cDNA for each of the HLA molecules which could present the antigen (A1, B37, Cw6) was used, separately, to cotransfect the cells. Specifically, one of 28 ng of the gene encoding HLA-A1, cloned into pCD-SRα 50 ng of cDNA for HLA-B37 in pcDNA-I-Amp, or 75 ng of cDNA for HLA-Cw6 in pcDNA-I-Amp, using the same protocol as was used for transfection with the library, were used.

Transfection was carried out in duplicate wells, but only 500 pools of the HLA-Cw6 transfectants could be tested in single wells. Following four hours of incubation at 37° C., the medium was removed, and replaced by 50 μl of PBS containing 10% DMSO. This medium was removed after two minutes and replaced by 200 μl of DMEM supplemented with 10% FCS.

Following this change in medium, COS cells were incubated for 24–48 hours at 37° C. Medium was then discarded, and 1000–3000 cells of CTL clone 76/6 were added, in 100 μl of Iscove's medium containing 10% pooled human serum supplemented with 20–30 U/ml of IL-2. Supernatant was removed after 24 hours, and TNF content was determined in an assay on WEHI cells, as described by Traversari et al., Immunogenetics 35: 145–152 (1992), the disclosure of which is incorporated by reference.

The 1500 pools transfected with HLA-A1, and the 1500 pools transfected with HLA-B37 stimulated TNF release to a concentration of 15–20 pg/ml, or 2–6 pg/ml, respectively. Most of the HLA-Cw6 transfectants yielded 3–20 pg/ml, except for one pool, which yielded more than 60 pg/ml. This pool was selected for further work.

Example 5

The bacteria of the selected pool were cloned, and 600 clones were tested. Plasmid DNA was extracted therefrom, transfected into a new sample of COS cells in the same manner as described supra, and the cells were again tested for stimulation of CTL clone 76/6. Ninety-four-positive clones were found. One of these, referred to as cDNA clone 2D6, was tested further. In a comparative test COS cells were transfected with cDNA clone 2D6 and the HLA-Cw6 cDNA, HLA-Cw6 cDNA alone, or cDNA 2D6 alone. Control cell lines MZ2-MEL F⁻ and MZ2-MEL F⁺ were also used. TNF release into CTL supernatant was measured by testing it on WEHI cells, as referred to supra. The number of surviving WEHI cells was measured by optical density after incubation of the cells with MTT. FIG. 2 shows that the COS cells transfected with HLA-Cw6 and cDNA-2D6, and the cell line MZ2-MEL F⁺ stimulated TNF release from CTL clone 76/6, indicating that HLA-Cw6 presented the subject TRA.

Example 6

The CDNA 2D6 was sequenced following art known techniques. A sequence search revealed that the plasmid insert showed no homology to known genes or proteins. SEQ ID NO: 1 presents CDNA nucleotide information for the identified gene, referred to hereafter as "GAGE". A putative open reading frame is located at bases 51–467 of the molecule. The first two bases of this sequence are from the vector carrying the CDNA sequence, and are thus not part of the cDNA itself.

Example 7

Following sequencing of the cDNA, as per Example 6, experiments were carried out to determine if cells of normal tissues expressed the gene. To determine this, Northern blotting was carried out on tissues and tumor cell lines, as indicated below. The blotting experiments used cDNA for the complete sequence of SEQ ID NO: 1. PCR was then used to confirm the results.

TABLE 1

| Expression of gene GAGE | |
|---|---|
| Normal tissues | |
| PHA activated T cells | – |
| CTL clone 82/30 | – |
| Liver | – |
| Muscle | – |
| Lung | – |
| Brain | – |
| Kidney | – |
| Placenta | – |
| Heart | – |
| Skin | –Testis+ |
| Tumor cell lines | |
| Melanoma | 7/16 |
| Lung Carcinoma | 1/6 |
| Sarcoma | 0/1 |
| Thyroid medullary carcinoma | 0/1 |
| Tumor samples | |
| Melanoma | 1/1 |

Example 8

Detailed analysis of normal tissues and tumors was carried out by applying polymerase chain reaction ("PCR") and the GAGE gene information described supra.

First, total RNA was taken from the particular sample, using art recognized techniques. This was used to prepare cDNA. The protocol used to make the cDNA involved combining 4 ul of reverse transcriptase buffer 5×, 1 ul of each dNTP, (10 mM), 2 ul of dithiothreitol (100 mM), 2 ul of dT-15 primer (20 um), 0.5 ul of RNasin (40 units/ul), and 1 ul of MOMLV reverse transcriptase (200 units/ul). Next, 6.5 ul of template RNA (1 ug/3.25 ul water, or 2 ug total template RNA) was added. The total volume of the mixture was 20 ul. This was mixed and incubated at 42° C. for 60 minutes, after which it was chilled on ice. A total of 80 ul of water was then added, to 100 ul total. This mixture was stored at −20° C. until used in PCR.

To carry out PCR, the primers

5'-AGA CGC TAC GTA GAG CCT-3'

(sense)
and

5'-CCA TCA GGA CCA TCT TCA-3'

(antisense).

SEQ ID NOS: 2 and 3, respectively, were used. The reagents included 30.5 ul water, 5 ul of PCR buffer 10×, 1 ul of each dNTP (10 uM), 2.5 ul of each primer (20 uM), and 0.5 ul of polymerizing enzyme Dynazyme (2 units/ul). The total volume was 45 ul. A total of 5 ul of cDNA was added (this corresponded to 100 ng total RNA). The mixture was combined, and layered with one drop of mineral oil. The mixture was transferred to a thermocycler block, preheated to 94° C., and amplification was carried out for 30 cycles, each cycle consisting of the following:

| first denaturation: | 94° C., 4 min. |
|---|---|
| denaturation: | 94° C., 1 min. |
| annealing: | 55° C., 2 min. |
| extension: | 72° C., 3 min. |
| final extension: | 72° C., 15 min. |

Following the cycling, 10 ul aliquots were run on a 1.5% agarose gel, stained with ethidium bromide.

CDNA amplified using the primers set forth supra yields a 238 base pair fragment. There is no amplification of contaminating genomic DNA, if present.

The results are presented in Table 2, which follows. They confirm that the only normal tissue which expresses GAGE is testis, whereas a number of tumors, including melanoma, lung, breast, larynx, pharynx, sarcoma, testicular seminoma, bladder and colon express the gene. Thus, any one of these tumors can be assayed for by assaying for expression of the GAGE gene.

TABLE 2

RT-PCR analysis of the expression of gene GAGE

NORMAL TISSUES

| Heart | − |
|---|---|
| Brain | − |
| Liver | − |
| Lung | − |
| Kidney | − |
| Spleen | − |
| Lymphocytes | − |
| Bone marrow | − |
| Skin | − |
| Naevus | − |
| Melanocytes | − |
| Fibroblasts | − |
| Prostate | − |
| Testis | + |
| Ovary | − |
| Breast | − |
| Adrenals | − |
| Muscle | − |
| Placenta | − |
| Umbilical Cord | − |

| TUMORS | Cell lines | Tumor samples | |
|---|---|---|---|
| Melanoma | 40/63 | 46/146 | (32%) |
| Lung cancer | | | |
| Epidermoid carcinoma | | 10/41 | (24%) |
| Adenocarcinoma | | 4/18 | |
| Small Cell Lung Cancer | 6/23 | 0/2 | |
| Breast cancer | | 15/146 | (10%) |
| Head and Neck tumor | | | |
| Larynx | | 6/15 | (40%) |
| Pharynx | | 3/13 | |
| Sarcoma | 1/4 | 6/18 | (33%) |
| Testicular seminoma | | 6/6 | (100%) |
| Bladder cancer | | 2/20 | |
| Prostate cancer | | 2/20 | |
| Colon carcinoma | 5/13 | 0/38 | |
| Renal cancer | 0/6 | 0/45 | |
| Leukemia | 3/6 | 0/19 | |

Example 9

The identification of the nucleic acid molecule referred to in the prior examples led to further work directed to the determination of tumor rejection antigens presented by HLA-Cw6 molecules, and derived from the GAGE gene.

The complete CDNA of GAGE in expression vector pcDNAI/Amp was digested with restriction endonucleases NotI and SpHI, and then with exonuclease III following supplier's instruction (Erase-a-base System, Promega). This treatment generated a series of progressive deletions, starting at the 3'end.

The deletion products were ligated back into pcDNAI/Amp, and then electroporated into E. coli strain DH5alpha'IQ, using well known techniques. The transformants were selected with ampicillin (50 micrograms/ml).

Plasmid DNA was extracted from each recombinant clone and was then transfected into COS-7 cells, together with a vector which coded for HLA-Cw6. The protocols used follow the protocols described above.

The transfectants were then tested in the TNF release assay. This permitted separation of positive and negative clones. All the negative clones showed a deletion of the entire GAGE sequence. The smallest positive clone contained the first 170 nucleotides of SEQ ID NO: 1. The analysis of this sequence, supra, notes that the open reading frame starts at nucleotide 51. Thus, this fragment contains a sequence which encodes the first 40 amino acids of the GAGE TRAP.

Example 10

Additional experiments were then carried out to define the region encoding the TRA peptide more precisely. Polymerase chain reaction ("PCR") amplification was used to do this.

Two primers were synthesized. The first primer was a 22-mer complementary to a sequence within the plasmid vector pcDNAI/Amp located upstream of a BamHI site. The second primer was a 29-mer containing at the 3'end nucleotides 102–119 of SEQ ID NO: 1, and at the 5'end an extension of 11 nucleotides containing an XbaI restriction site.

Following amplification, the PCR product was digested by BamHI and XbaI, and cloned into the BamHI-XbaI sites of plasmid pcDNA-3. The recombinant colonies were cotransfected into COS-7 cells with cDNA encoding HLA-Cw6, in accordance with Example 4, and a TNF release assay, also as described supra, was carried out, using CTL 76/6.

TNF release was observed, indicating that the "minigene" was processed to a TRA. The minigene, i.e., nucleotides 1–119 of SEQ ID NO: 1, the coding region of which runs from nucleotides 51–119 encoded the first 23 amino acids of the cDNA of SEQ ID NO: 1. This information served as the basis for the next set of experiments.

Example 11

Two peptides were synthesized, based upon the first 23 amino acids of SEQ ID NO: 1. These were:

Met Ser Trp Arg Gly Arg Ser Thr Tyr Arg Pro Arg Pro Arg Arg (SEQ ID NO: 12)

and

Thr Tyr Arg Pro Arg Pro Arg Arg Tyr Val Glu Pro Pro Glu Met Ile (SEQ ID NO: 13)

Each peptide was pulsed into COS-7 cells previously transfected with HLA-Cw6 cDNA, and combined with CTL 76/6 to determine if TNF release would be induced. Peptides (20 ug/ml) were added to COS-7 cells which had been transfected with the HLA-Cw6 cDNA twenty-four hours previously. After incubation at 37° C. for 90 minutes, medium was discarded, and 3000 CTLs were added in 100 microliters of medium, containing 25 units/ml of IL-2. Eighteen hours later, TNF content of supernatant was tested via determining toxicity on WEHI-164–13 cells. The second peptide (SEQ ID NO: 13) was found to induce more than 30 pg/ml of TNF, while the first peptide (SEQ ID NO: 12), was found to induce less than 10 pg/ml of TNF. The second peptide was used for further experiments.

Example 12

Various peptides based upon SEQ ID NO: 13 were synthesized, and tested, some of which are presented below. To carry out these tests, $^{51}$Cr labelled LB33-EBV cells, which are HLA-Cw6 positive, were incubated with one of the following peptides: 1

```
Tyr Arg Pro Arg Pro Arg Arg Tyr        (SEQ ID NO: 4)

Thr Tyr Arg Pro Arg Pro Arg Arg Tyr    (SEQ ID NO: 5)

Tyr Arg Pro Arg Pro Arg Arg Tyr Val    (SEQ ID NO: 6)

Thr Tyr Arg Pro Arg Pro Arg Arg Tyr-   (SEQ ID NO: 7)
 Val

Arg Pro Arg Pro Arg Arg Tyr Val Glu    (SEQ ID NO: 8)

Met Ser Trp Arg Gly Arg Ser Thr-       (SEQ ID NO:12)
 Tyr Arg

Pro Arg Pro Arg Arg

0
```

Figure 3:
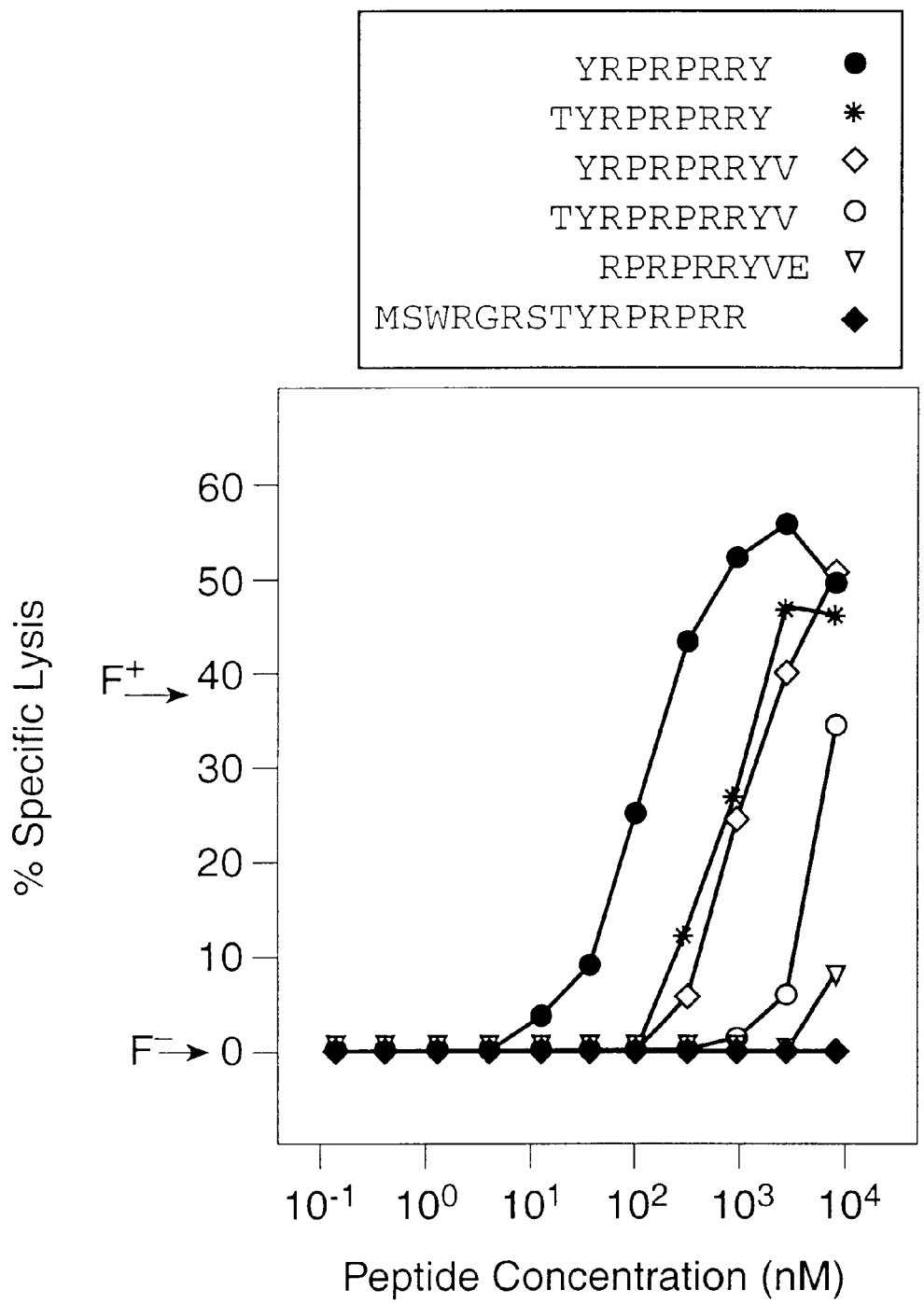
FIG. 3 compares lysis induced by cytolytic T lymphocytes of clone CTL 76/6. Peptides of varying length were tested, including SEQ ID NOS: 4–8 and 12.
Figure 6:
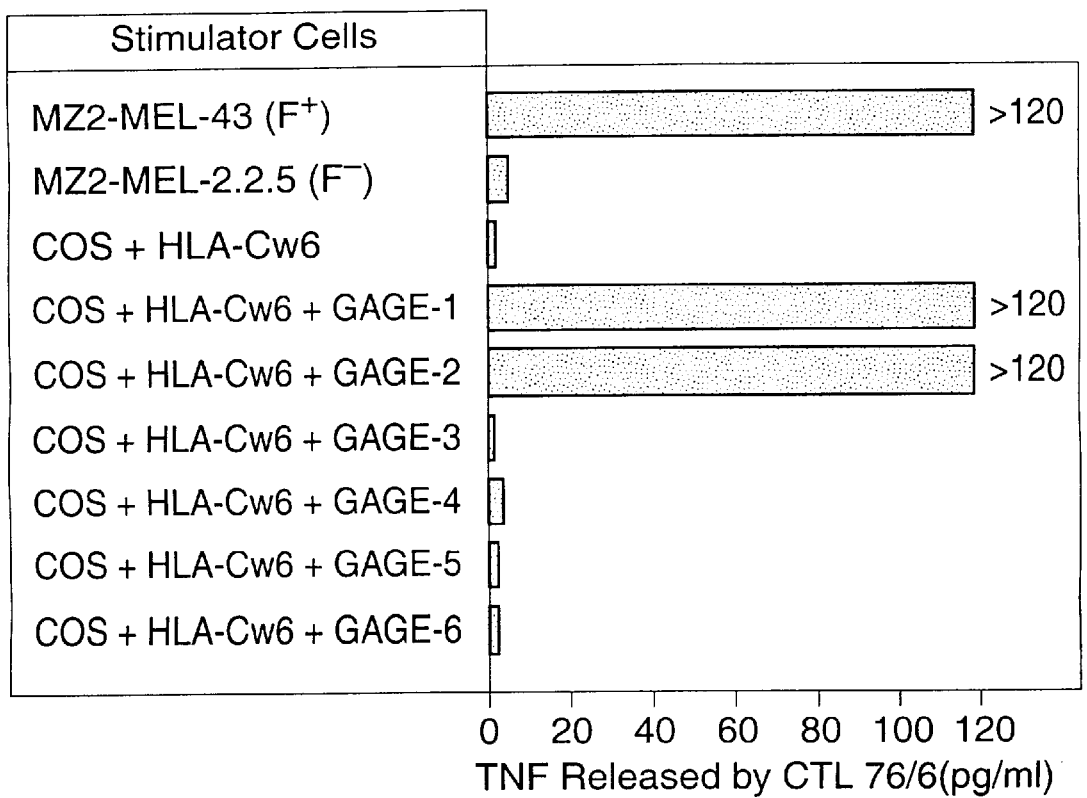
FIG. 6 shows the results obtained when each of the GAGE cDNAs was transfected into COS cells, together with HLA-Cw6 cDNA. Twenty-four hours later, samples of CTL 76/6 were added, and TNF release was measured after twenty-four hours.

The peptide concentration varied, as indicated in FIG. 3, and the ratio of CTL: LB33-EBV ("effector: target ratio"), was 10:1. $^5$Cr release was determined after four hours of incubation at 37° C. Levels of lysis for positive ("F⁺", MZ2-MEL.3.1), and negative ("F⁻"; MZ2-MEL.2.2.5) control cells are indicated, in FIG. 3.

It was found, quite surprisingly, that the octamer of SEQ ID NO: 4 was the best peptide, and appeared to be the tumor rejection antigen. This is the first time an octamer has been reported as being involved in presentation by a human MHC molecule. There is some precedent for a murine system, as reported by Engelhard, supra, at 199, for H-2K$^b$ and H-2K$^K$ molecules. The nonamers of SEQ ID NO: 5 and SEQ ID NO: 6 also induced CTL lysis albeit to a lesser extent than the octamer of SEQ ID NO: 4.

In results not reported here, a second CTL was tested (CTL 82/31). This CTL was known to lyse cells presenting MZ2-F. It, too, lysed HLA-Cw6 positive cells following pulsing with the peptide of SEQ ID NO: 4.

Example 13

Figure 4A:
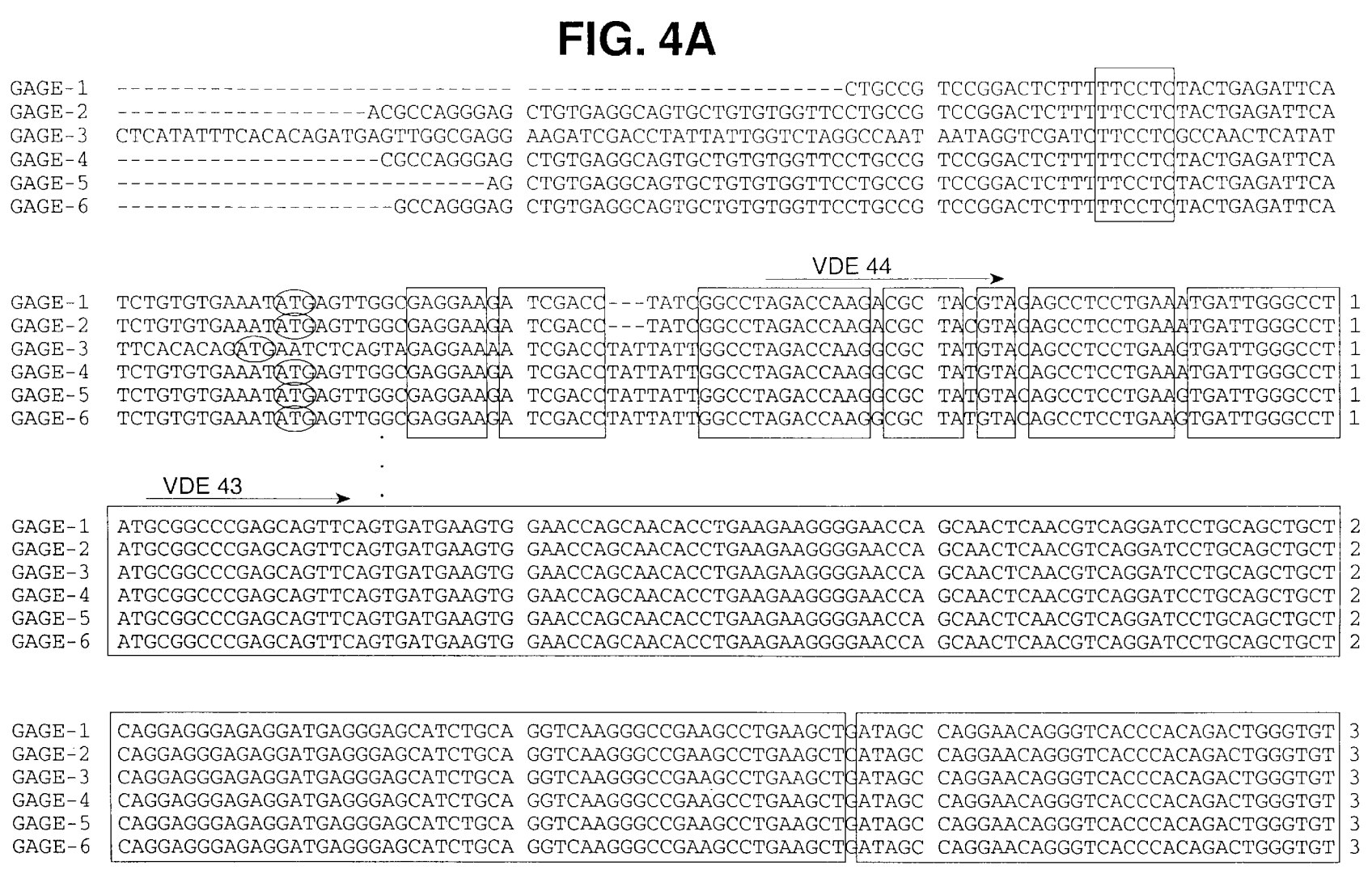
Figure 4B:
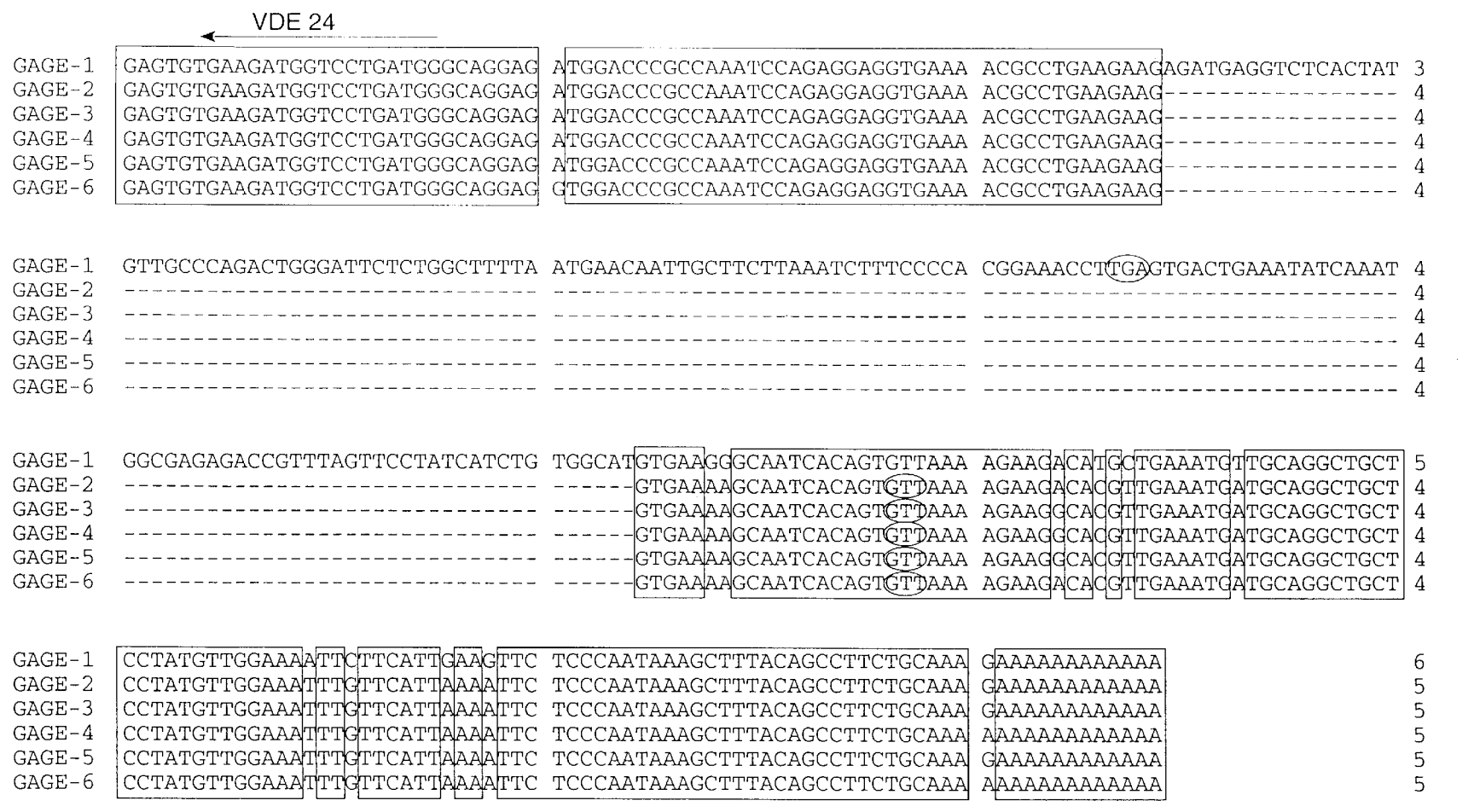

To find out whether the GAGE DNA set forth supra was unique, a cDNA library made with RNA from MZ2-MEL.43 (the same library that was used for the cloning of GAGE) was hybridized with a probe derived from the GAGE CDNA. The probe was a PCR fragment of 308 base pairs between positions 20 and 328 of SEQ ID NO: 1. Twenty positive cDNAs were obtained. Six of them were entirely sequenced. They were all highly related to the GAGE sequence, but they were slightly different from it. Two of the six clones were identical to each other, but all the others differed from each other. Thus, five new sequences different from but highly related to GAGE were identified. They are called GAGE-2, 3, 4, 5 and 6 (FIG. 4), and are presented as SEQ ID NOS: 14–18, respectively. The fourteen other clones were partially sequenced at the 5' end and their sequence corresponded to one of the six GAGE cDNAs.

The major difference between these cDNAs and GAGE-1 is the absence of a stretch of 143 bases located at position 379 to 521 of the GAGE sequence of SEQ ID NO: 1. The rest of the sequences shows mismatches only at 19 different positions, with the exception of GAGE-3 whose 5'end is totally different from the other GAGE for the first 112 bases. This region of the GAGE-3 cDNA contains a long repeat and a hairpin structure.

The deduced GAGE-1 protein corresponding to a tumor rejection antigen precursor is about 20 amino acids longer than the 5 other proteins, whose last seven residues also differ from the homologous residues of GAGE-1 (FIG. 5). The rest of the protein sequences show only 10 mismatches. One of these is in the region corresponding to the antigenic peptide of SEQ ID NO: 4. The sequence of the peptide is modified in GAGE-3, 4, 5 and 6 so that position 2 is now W instead of R.

Example 14

To assess whether the change at position 2 affected the antigenicity of the peptide, cDNA of the 6 GAGE cDNAs were individually transfected into COS cells together with the CDNA of HLA-Cw6, and the transfectants were tested for recognition by CTL 76/6 as described, supra. Only GAGE-1 and GAGE-2 transfected cells were recognized, showing that the modified peptide encoded by GAGE-3, 4, 5 and 6 was not antigenic in the context of this experiment. Sequence analysis of the 5' end of the 14 other clones mentioned supra, showed that 7 of them contained the sequence encoding the antigenic peptide, and thus probably corresponded to either GAGE-1 or GAGE-2.

Example 15

The PCR primers used, supra to test the expression of GAGE in tumor samples do not discriminate between GAGE-1 or 2 and the four other GAGE cDNAs that do not encode antigen MZ2F. A new set of primers was prepared which specifically amplifies GAGE-1 and 2, and not GAGE-3, 4, 5 and 6. These primers are:

VDE44 5'-GAC CAA GAC GCT ACG TAG-3' (SEQ ID NO: 9)

VDE24 5'-CCA TCA GGA CCA TCT TCA-3' (SEQ ID NO: 10)

These primers were used as described, supra, in a RT-PCR reaction using a polymerase enzyme in the following temperature conditions:

| 4 min at 94° C. | |
|---|---|
| 30 cycles with | 1 min at 94° C. |
| | 2 min at 56° C. |
| | 3 min at 72° C. |
| 15 min at 72° C. | |

The results of this analysis are set forth in Table 3.

TABLE 3

Expression of GAGE genes by tumor samples and tumor cell lines

| Histological type | Number of GAGE positive tumors | |
|---|---|---|
| | All GAGE genes* | GAGE-1 and 2** |
| Tumor samples | | |
| Melanomas | | |
| primary lesions | 5/39 | 5/39 (13%) |
| metastases | 47/132 | 36/131 (27%) |
| Sarcomas | 6/20 | 6/20 (30%) |
| Lung carcinomas NSCLC | 14/65 | 12/64 (19%) |
| Head and neck squamous cell carcinomas | 13/55 | 10/54 (19%) |
| Prostatic carcinomas | 2/20 | 2/20 |
| Mammary carcinomas | 18/162 | 14/162 (9%) |
| Bladder carcinomas | | |
| superficial | 1/20 | 1/20 |
| infiltrating | 5/26 | 3/26 |
| Testicular seminomas | 6/6 | 5/6 |
| Colorectal carcinomas | 0/43 | |
| Leukemias and lymphomas | 0/25 | |
| Renal carcinomas | 0/46 | |
| Tumor cell lines | | |
| Melanomas | 45/74 | 40/74 (54%) |
| Sarcomas | 1/4 | 1/4 |
| Lung carcinomas | | |
| SCLC | 7/24 | 7/24 (29%) |
| NSCLC | 1/2 | 1/2 |
| Mesotheliomas | 5/19 | 5/19 (26%) |
| Head and neck squamous cell carcinomas | 0/2 | |
| Mammary carcinomas | 1/4 | 0/4 |
| Bladder carcinomas | 0/3 | |
| Colon carcinomas | 5/13 | 5/13 |
| Leukemias | 3/6 | 1/6 |
| Lymphomas | 0/6 | |
| Renal carcinomas | 0/6 | |

*Expression of GAGE was tested by RT-PCR on total RNA with primers VDE-18 and VDE-24, detecting all GAGE genes. No PCR product was observed when these primers were assayed on DNA from MZ2-MEL.
**Expression of GAGE-1 and 2 was tested by RT-PCR on total RNA with primers VDE-44 and VDE-24, which distinguish GAGE-1 and 2 from the four other GAGE genes. No PCR product was observed when these primers were assayed on DNA from MZ2-MEL.

In further work, new primers were designed which amplified all GAGE genes, to make sure that there was no expression of any of them in normal tissues. These primers are

VDE43 5'-GCG GCC CGA GCA GTT CA-3' (SEQ ID NO: 11)

VDE24 5'-CCA TCA GGA CCA TCT TCA-3 (SEQ ID NO: 10)

These were used exactly as for the PCR using the VDE44 and VDE24 primers. The results are shown in Table 4. They confirm that the normal tissues are negative, except for testis.

TABLE 4

Expression of GAGE genes in normal adult and fetal tissues

| | GAGE expression* |
|---|---|
| Adult tissues | |
| Adrenal gland | − |
| Benign naevus | − |
| Bone marrow | − |
| Brain | − |
| Breast | − |
| Cerebellum | − |
| Colon | − |
| Heart | − |
| Kidney | − |
| Liver | − |
| Lung | − |
| Melanocytes | − |
| Muscle | − |
| Ovary | − |
| Prostate | − |
| Skin | − |
| Splenocytes | − |
| Stomach | − |
| Testis | + |
| Thymocytes | − |
| Urinal bladder | − |
| Uterus | − |
| Placenta | − |
| Umbilical cord | − |
| Fetal tissues• | |
| Fibroblasts | − |
| Brain | − |
| Liver | − |
| Spleen | − |
| Thymus | − |
| Testis | + |

*Expression of GAGE was tested by RT-PCR amplification on total RNA with primers VDE43 and VDE24 detecting all GAGE genes (FIG. 7). Absence of PCR product is indicated by − and presence by +. No PCR product was observed when these primers were assayed on DNA from MZ2-MEL.
•Fetal tissues derive from fetuses older than 20 weeks.

The foregoing examples show the isolation of nucleic acid molecules which code for tumor rejection antigen precursors and tumor rejection antigens. These molecules, however, are not homologous with any of the previously disclosed MAGE and BAGE coding sequences described in the references set forth supra. Hence, one aspect of the invention is an isolated nucleic acid molecule which comprises the nucleotide sequence set forth in SEQ ID NO: 1 as well as fragments thereof, such as nucleotides 1–170, and 51–170, and any other fragment which is processed to a tumor rejection antigen. The sequence of SEQ ID NO: 1 is neither a MAGE nor a BAGE coding sequence, as will be seen by comparing it to the sequence of any of these genes as described in the cited references. Also a part of the invention are those nucleic acid molecules which also code for a non-MAGE and non-BAGE tumor rejection antigen precursor but which hybridize to a nucleic acid molecule containing the described nucleotide sequence, under stringent conditions. The term "stringent conditions" as used herein refers to parameters with which the art is familiar. More specifically, stringent conditions, as used herein, refers to hybridization in 1M NaCl, 1% SDS, and 10% dextran sulfate. This is followed by two washes of the filter at room temperature for 5 minutes, in 2× SSC, and one wash for 30 minutes in 2× SSC, 0.1% SDS. There are other conditions, reagents, and so forth which can be used, which result in the same or higher degree of stringency. The skilled artisan will be familiar with such conditions, and, thus, they are not given here.

It will also be seen from the examples that the invention embraces the use of the sequences in expression vectors, as well as to transform or transfect host cells and cell lines, be these prokaryotic (e.g., *E. coli*), or eukaryotic (e.g., CHO or COS cells). The expression vectors require that the pertinent sequence, i.e., those described supra, be operably linked to a promoter. As it has been found that human leukocyte antigen HLA-Cw6 presents a tumor rejection antigen derived from these genes, the expression vector may also include a nucleic acid molecule coding for HLA-Cw6. In a situation where the vector contains both coding sequences, it can be used to transfect a cell which does not normally express either one. The tumor rejection antigen precursor coding sequence may be used alone, when, e.g., the host cell already expresses HLA-Cw6. Of course, there is no limit on the particular host cell which can be used. As the vectors which contain the two coding sequences may be used in HLA-Cw6 presenting cells if desired, and the gene for tumor rejection antigen precursor can be used in host cells which do not express HLA-Cw6.

The invention also embraces so called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

To distinguish the nucleic acid molecules and the TRAPs of the invention from the previously described MAGE and BAGE materials, the invention shall be referred to as the GAGE family of genes and TRAPs. Hence, whenever "GAGE" is used herein, it refers to the tumor rejection antigen precursors coded for by the previously described sequences. "GAGE coding molecule" and similar terms, are used to describe the nucleic acid molecules themselves.

The invention as described herein has a number of uses, some of which are described herein. First, the invention permits the artisan to diagnose a disorder such as melanoma, characterized by expression of the TRAP, or presentation of the tumor rejection antigen. These methods involve determining expression of the TRAP gene, and/or TRAs derived therefrom, such as a TRA presented by HLA-Cw6. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred. An alternate method for determination is a TNF release assay, of the type described supra. To carry out the assay, it is preferred to make sure that testis cells are not present, as these normally express GAGE. This is not essential, however, as one can routinely differentiate between testis and other cell types. Also, it is practically impossible to have testis cells present in non-testicular sample.

The isolation of the TRAP gene also makes it possible to isolate the TRAP molecule itself, especially TRAP molecules containing the amino acid sequence coded for by SEQ ID NO: 1. These isolated molecules when presented as the TRA, or as complexes of TRA and HLA, such as HLA-Cw6, may be combined with materials such as adjuvants to produce vaccines useful in treating disorders characterized by expression of the TRAP molecule. In addition, vaccines can be prepared from cells which present the TRA/HLA complexes on their surface, such as nonproliferative cancer cells, non-proliferative transfectants, et cetera. In all cases where cells are used as a vaccine, these can be cells transfected with coding sequences for one or both of the components necessary to provide a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular. Melanoma is well known as a cancer of pigment producing cells.

As indicated, supra, tumor rejection antigens, such as the one presented in SEQ ID NO: 4 are also a part of the invention. Also a part of the invention are polypeptides, such as molecules containing from 8 to 16 amino acids, where the polypeptides contain the amino acid sequence set forth in SEQ ID NO: 4. As the examples indicate, those peptides which are longer than the octamer of SEQ ID NO: 4 are processed into the tumor rejection antigen of SEQ ID NO: 4 by the HLA-Cw6 presenting cancer cells, and presented thereby. The presentation leads to lysis by cytolytic T lymphocytes present in a body fluid sample contacted to the cells presenting the complex. The fact that these peptides are processed to the tumor rejection antigen, is indicated by the examples.

This property may be exploited in the context of other parameters in confirming diagnosis of pathological conditions, such as cancer, melanoma in particular. For example, the investigator may study antigens shed into blood or urine, observe physiological changes, and then confirm a diagnosis of melanoma using the CTL proliferation methodologies described herein.

On their own, peptides in accordance with the invention may be used to carry out HLA-typing assays. It is well known that when a skin graft, organ transplant, etc., is necessary one must perform HLA typing so as to minimize the possibility of graft rejection. The peptides of the invention may be used to determine whether or not an individual is HLA-Cw6 positive, so that appropriate donors may be selected. This type of assay is simple to carry out. The peptides of the invention are contacted to a sample of interest, and binding to cells in that sample indicates whether or not the individual from which the sample is taken is HLA-Cw6 positive. One may label the peptides themselves, conjugate or otherwise bind them to linkers which are labeled, immobilize them to solid phases, and so forth, so as to optimize such an assay. Other standard methodologies will be clear to the skilled artisan, and need not be presented herein.

Therapeutic approaches based upon the disclosure are premised on a response by a subject's immune system, leading to lysis of TRA presenting cells, such as HLA-Cw6 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917

(1986); Riddel et al., Science 257: 238 (Jul. 10, 1992); Lynch et al., Eur. J. Immunol. 21: 1403–1410 (1991); Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex, where the complex contains the pertinent HLA molecule. The CTLs then lyse the abnormal cells, thereby achieving the desired therapeutic goal.

The foregoing therapy assumes that at least some of the subject's abnormal cells present the relevant HLA/TRA complex. This can be determined very easily, as the art is very familiar with methods for identifying cells which present a particular HLA molecule, as well as how to identify cells expressing RNA of the pertinent sequences, in this case a GAGE sequence. Once cells presenting the relevant complex are identified via the foregoing screening methodology, they can be combined with a sample from a patient, where the sample contains CTLs. If the complex presenting cells are lysed by the mixed CTL sample, then it can be assumed that a GAGE derived, tumor rejection antigen is being presented, and the subject is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPV E7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-Cw6 presenting cells which then present the HLA/peptide complex of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated nucleic acid molecule consisting of nucleotides 1–170 of SEQ ID NO: 1.
2. Isolated nucleic acid molecule consisting of nucleotides 1–119 of SEQ ID NO: 1.
3. Expression vector comprising the isolated nucleic acid molecule of claim 1, operably linked to a promoter.
4. Cell line comprising the isolated nucleic acid molecule of claim 1.
5. Cell line comprising the expression vector of claim 3.
6. Isolated nucleic acid molecule consisting of nucleotides 51–170 of SEQ ID NO: 1.
7. Expression vector comprising the isolated nucleic acid molecule of claim 6, operably linked to a promoter.
8. Cell line comprising the isolated nucleic acid molecule of claim 6.
9. Cell line comprising the expression vector of claim 7.
10. The cell line of claim 4, 5, 8 or 9, wherein said cell line expresses an HLA-Cw6 molecule.
11. The cell line of claim 9 wherein said cell line has been transfected with a nucleic acid molecule which codes for HLA-Cw6.
12. Biologically pure prokaryotic cell transformed with the nucleic acid molecule of claim 6.
13. Biologically pure prokaryotic cell transformed with the expression vector of claim 7.

* * * * *

UNITED STATES PATENT AND TRADEMARK OFFICE
CERTIFICATE OF CORRECTION

PATENT NO. : 6,069,001
DATED : May 30, 2000
INVENTOR(S) : Van den Eynde et al

It is certified that error appears in the above-identified patent and that said Letters Patent is hereby corrected as shown below:

In column 4, line 46, change "MRNA" to -- MRNA --.
In column 4, line 49, change "CDNA" to -- cDNA --.
In column 5, line 62, change "CDNA" to -- cDNA --.
In column 5, line 66, change "CDNA" to -- cDNA --.
In column 6, line 2, after "experiments" delete -- - --.
In column 6, Table 1, column 2, line 23, delete -- Testis+ --.
In column 6, Table 1, column 2, line 24, insert -- Testis    + --.
In column 7, line 14, change "CDNA" to -- cDNA --.
In column 7, Table 2, change "Bladder cancer    2/20" to
-- Bladder cancer         5/37       (14%) --.
In column 8, line 3, change "CDNA" to -- cDNA --.
In column 69 line 34, delete -- 0 --.
In column 9, line 58, change "CDNA" to -- cDNA --.
In column 9, line 61, change "CDNA" to -- cDNA --.
In column 10, line 32, change "CDNA" to -- cDNA --.

Signed and Sealed this

Fifteenth Day of May, 2001

Attest:

NICHOLAS P. GODICI

Attesting Officer      Acting Director of the United States Patent and Trademark Office

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 646 base pairs
        (B) TYPE: nucleic acid
        (C) STRANDEDNESS: single
        (D) TOPOLOGY: linear (xi) SEQUENCE DESCRIPTION: SEQ ID NO:1:

```
CTGCCGTCCG GACTCTTTTT CCTCTACTGA GATTCATCTG TGTGAAATAT          50

GAGTTGGCGA GGAAGATCGA CCTATCGGCC TAGACCAAGA CGCTACGTAG         100

AGCCTCCTGA AATGATTGGG CCTATGCGGC CCGAGCAGTT CAGTGATGAA         150

GTGGAACCAG CAACACCTGA AGAAGGGGAA CCAGCAACTC AACGTCAGGA         200

TCCTGCAGCT GCTCAGGAGG GAGAGGATGA GGGAGCATCT GCAGGTCAAG         250

GGCCGAAGCC TGAAGCTGAT AGCCAGGAAC AGGGTCACCC ACAGACTGGG         300

TGTGAGTGTG AAGATGGTCC TGATGGGCAG GAGATGGACC CGCCAAATCC         350

AGAGGAGGTG AAAACGCCTG AAGAAGAGAT GAGGTCTCAC TATGTTGCCC         400

AGACTGGGAT TCTCTGGCTT TTAATGAACA ATTGCTTCTT AAATCTTTCC         450

CCACGGAAAC CTTGAGTGAC TGAAATATCA AATGGCGAGA GACCGTTTAG         500

TTCCTATCAT CTGTGGCATG TGAAGGGCAA TCACAGTGTT AAAAGAAGAC         550
```

```
ATGCTGAAAT GTTGCAGGCT GCTCCTATGT TGGAAAATTC TTCATTGAAG            600

TTCTCCCAAT AAAGCTTTAC AGCCTTCTGC AAAGAAAAAA AAAAAA               646
```

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 2:

```
AGACGCTACG TAGAGCCT                                              18
```

(2) INFORMATION FOR SEQ ID NO: 3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 3:

```
CCATCAGGAC CATCTTCA                                              18
```

(2) INFORMATION FOR SEQ ID NO: 4:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO: 4:

```
Tyr Arg Pro Arg Pro Arg Arg Tyr
                5
```

(2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 5:

```
Thr Tyr Arg Pro Arg Pro Arg Arg Tyr
                5
```

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 6:

```
Tyr Arg Pro Arg Pro Arg Arg Tyr Val
                5
```

(2) INFORMATION FOR SEQ ID NO: 7:

(i) SEQUENCE CHARACTERISTICS:
        (A) LENGTH: 10 amino acids
        (B) TYPE: amino acid
        (D) TOPOLOGY: linear (xi) SEQUENCE DESCRIPTION: SEQ ID NO: 7:

Thr Tyr Arg Pro Arg Pro Arg Arg Tyr Val
            5                   10

(2) INFORMATION FOR SEQ ID NO: 8:

(i) SEQUENCE CHARACTERISTICS:
        (A) LENGTH: 9 amino acids
        (B) TYPE: amino acid
        (D) TOPOLOGY: linear (xi) SEQUENCE DESCRIPTION: SEQ ID NO: 8:

Arg Pro Arg Pro Arg Arg Tyr Val Glu
            5

(2) INFORMATION FOR SEQ ID NO: 9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 9:

GACCAAGACG CTACGTAG                                                   18

(2) INFORMATION FOR SEQ ID NO: 10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 10:

CCATCAGGAC CATCTTCA                                                   18

(2) INFORMATION FOR SEQ ID NO: 11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 11:

GCGGCCCGAG CAGTTCA                                                    17

(2) INFORMATION FOR SEQ ID NO: 12:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO: 12:

Met Ser Trp Arg Gly Arg Ser Thr Tyr Arg Pro Arg Pro Arg Arg
            5                   10                  15

(2) INFORMATION FOR SEQ ID NO: 13:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 13:

Thr Tyr Arg Pro Arg Pro Arg Arg Tyr Val Glu Pro Pro Glu Met Ile (2) INFORMATION FOR SEQ ID NO: 14:

(i) SEQUENCE CHARACTERISTICS:
        (A) LENGTH: 538 base pairs
        (B) TYPE: nucleic acid
        (C) STRANDEDNESS: single
        (D) TOPOLOGY: linear (xi) SEQUENCE DESCRIPTION: SEQ ID NO: 14:

```
ACGCCAGGGA GCTGTGAGGC AGTGCTGTGT GGTTCCTGCC GTCCGGACTC         50

TTTTTCCTCT ACTGAGATTC ATCTGTGTGA AATATGAGTT GGCGAGGAAG        100

ATCGACCTAT CGGCCTAGAC CAAGACGCTA CGTAGAGCCT CCTGAAATGA        150

TTGGGCCTAT GCGGCCCGAG CAGTTCAGTG ATGAAGTGGA ACCAGCAACA        200

CCTGAAGAAG GGGAACCAGC AACTCAACGT CAGGATCCTG CAGCTGCTCA        250

GGAGGGAGAG GATGAGGGAG CATCTGCAGG TCAAGGGCCG AAGCCTGAAG        300

CTCATAGCCA GGAACAGGGT CACCCACAGA CTGGGTGTGA GTGTGAAGAT        350

GGTCCTGATG GGCAGGAGAT GGACCCGCCA AATCCAGAGG AGGTGAAAAC        400

GCCTGAAGAA GGTGAAAAGC AATCACAGTG TTAAAAGAAG ACACGTTGAA        450

ATGATGCAGG CTGCTCCTAT GTTGGAAATT TGTTCATTAA AATTCTCCCA        500

ATAAAGCTTT ACAGCCTTCT GCAAAGAAAA AAAAAAA                      538
```

(2) INFORMATION FOR SEQ ID NO: 15:

(i) SEQUENCE CHARACTERISTICS:
        (A) LENGTH: 560 base pairs
        (B) TYPE: nucleic acid
        (C) STRANDEDNESS: single
        (D) TOPOLOGY: linear (xi) SEQUENCE DESCRIPTION: SEQ ID NO: 15:

```
CTCATATTTC ACACAGATGA GTTGGCGAGG AAGATCGACC TATTATTGGT         50

CTAGGCCAAT AATAGGTCGA TCTTCCTCGC CAACTCATAT TTCACACAGA        100

TGAATCTCAG TAGAGGAAAA TCGACCTATT ATTGGCCTAG ACCAAGGCGC        150

TATGTACAGC CTCCTGAAGT GATTGGGCCT ATGCGGCCCG AGCAGTTCAG        200

TGATGAAGTG GAACCAGCAA CACCTGAAGA AGGGGAACCA GCAACTCAAC        250

GTCAGGATCC TGCAGCTGCT CAGGAGGGAG AGGATGAGGG AGCATCTGCA        300

GGTCAAGGGC CGAAGCCTGA AGCTGATAGC CAGGAACAGG GTCACCCACA        350

GACTGGGTGT GAGTGTGAAG ATGGTCCTGA TGGGCAGGAG ATGGACCCGC        400

CAAATCCAGA GGAGGTGAAA ACGCCTGAAG AAGGTGAAAA GCAATCACAG        450

TGTTAAAAGA AGGCACGTTG AAATGATGCA GGCTGCTCCT ATGTTGGAAA        500

TTTGTTCATT AAAATTCTCC CAATAAAGCT TTACAGCCTT CTGCAAAGAA        550

AAAAAAAAA                                                     560
```

(2) INFORMATION FOR SEQ ID NO: 16:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (xi) SEQUENCE DESCRIPTION: SEQ ID NO: 16:

| | |
|---|---|
| CGCCAGGGAG CTGTGAGGCA GTGCTGTGTG GTTCCTGCCG TCCGGACTCT | 50 |
| TTTTCCTCTA CTGAGATTCA TCTGTGTGAA ATATGAGTTG GCGAGGAAGA | 100 |
| TCGACCTATT ATTGGCCTAG ACCAAGGCGC TATGTACAGC CTCCTGAAAT | 150 |
| GATTGGGCCT ATGCGGCCCG AGCAGTTCAG TGATGAAGTG GAACCAGCAA | 200 |
| CACCTGAAGA AGGGGAACCA GCAACTCAAC GTCAGGATCC TGCAGCTGCT | 250 |
| CAGGAGGGAG AGGATGAGGG AGCATCTGCA GGTCAAGGGC CGAAGCCTGA | 300 |
| AGCTGATAGC CAGGAACAGG GTCACCCACA GACTGGGTGT GAGTGTGAAG | 350 |
| ATGGTCCTGA TGGGCAGGAG ATGGACCCGC CAAATCCAGA GGAGGTGAAA | 400 |
| ACGCCTGAAG AAGGTGAAAA GCAATCACAG TGTTAAAAGA AGGCACGTTG | 450 |
| AAATGATGCA GGCTGCTCCT ATGTTGGAAA TTTGTTCATT AAAATTCTCC | 500 |
| CAATAAAGCT TTACAGCCTT CTGCAAAAAA AAAAAAAAA | 540 |

(2) INFORMATION FOR SEQ ID NO: 17:

(i) SEQUENCE CHARACTERISTICS:
  (A) LENGTH: 532 base pairs
  (B) TYPE: nucleic acid
  (C) STRANDEDNESS: single
  (D) TOPOLOGY: linear (xi) SEQUENCE DESCRIPTION: SEQ ID NO: 17:

| | |
|---|---|
| AGCTGTGAGG CAGTGCTGTG TGGTTCCTGC CGTCCGGACT CTTTTTCCTC | 50 |
| TACTGAGATT CATCTGTGTG AAATATGAGT TGGCGAGGAA GATCGACCTA | 100 |
| TTATTGGCCT AGACCAAGGC GCTATGTACA GCCTCCTGAA GTGATTGGGC | 150 |
| CTATGCGGCC CGAGCAGTTC AGTGATGAAG TGGAACCAGC AACACCTGAA | 200 |
| GAAGGGGAAC CAGCAACTCA ACGTCAGGAT CCTGCAGCTG CTCAGGAGGG | 250 |
| AGAGGATGAG GGAGCATCTG CAGGTCAAGG GCCGAAGCCT GAAGCTGATA | 300 |
| GCCAGGAACA GGGTCACCCA CAGACTGGGT GTGAGTGTGA AGATGGTCCT | 350 |
| GATGGGCAGG AGATGGACCC GCCAAATCCA GAGGAGGTGA AAACGCCTGA | 400 |
| AGAAGGTGAA AAGCAATCAC AGTGTTAAAA GAAGGCACGT TGAAATGATG | 450 |
| CAGGCTGCTC CTATGTTGGA AATTTGTTCA TTAAAATTCT CCCAATAAAG | 500 |
| CTTTACAGCC TTCTGCAAAG AAAAAAAAAA AA | 532 |

(2) INFORMATION FOR SEQ ID NO: 18:

(i) SEQUENCE CHARACTERISTICS:
  (A) LENGTH: 539 base pairs
  (B) TYPE: nucleic acid
  (C) STRANDEDNESS: single
  (D) TOPOLOGY: linear (xi) SEQUENCE DESCRIPTION: SEQ ID NO: 18:

| | |
|---|---|
| GCCAGGGAGC TGTGAGGCAG TGCTGTGTGG TTCCTGCCGT CCGGACTCTT | 50 |
| TTTCCTCTAC TGAGATTCAT CTGTGTGAAA TATGAGTTGG CGAGGAAGAT | 100 |
| CGACCTATTA TTGGCCTAGA CCAAGGCGCT ATGTACAGCC TCCTGAAGTG | 150 |
| ATTGGGCCTA TGCGGCCCGA GCAGTTCAGT GATGAAGTGG AACCAGCAAC | 200 |
| ACCTGAAGAA GGGGAACCAG CAACTCAACG TCAGGATCCT GCAGCTGCTC | 250 |
| AGGAGGGAGA GGATGAGGGA GCATCTGCAG GTCAAGGGCC GAAGCCTGAA | 300 |

-continued

```
GCTGATAGCC AGGAACAGGG TCACCCACAG ACTGGGTGTG AGTGTGAAGA         350

TGGTCCTGAT GGGCAGGAGG TGGACCCGCC AAATCCAGAG GAGGTGAAAA         400

CGCCTGAAGA AGGTGAAAAG CAATCACAGT GTTAAAAGAA GACACGTTGA         450

AATGATGCAG GCTGCTCCTA TGTTGGAAAT TTGTTCATTA AAATTCTCCC         500

AATAAAGCTT TACAGCCTTC TGCAAAAAAA AAAAAAAA                      539
```